United States Patent
Matveld et al.

(10) Patent No.: US 6,348,336 B1
(45) Date of Patent: Feb. 19, 2002

(54) PROCESS FOR PURIFICATION OF PCR TEST SAMPLES

(75) Inventors: H. Edward Matveld, North Hollywood; Lorraine B. Peddada, Arcadia; Andrew J. Conrad, Los Angeles; Charles M. Heldebrant, Arcadia, all of CA (US)

(73) Assignee: Alpha Therapeutic Corporation, Los Angeles, CA (US)

( * ) Notice: Subject to any disclaimer, the term of this patent is extended or adjusted under 35 U.S.C. 154(b) by 0 days.

(21) Appl. No.: 08/886,330

(22) Filed: Jul. 1, 1997

(51) Int. Cl.$^7$ ................................................. C12P 19/34
(52) U.S. Cl. .......................... 435/91.2; 435/6; 435/91.1
(58) Field of Search ........................ 435/6, 91.1, 235.1, 435/239, 91.2; 536/23.1, 127

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 5,176,995 A | 1/1993 | Sninsky et al. | 435/6 |

OTHER PUBLICATIONS

Akane et al., J. Forensic Sci., 38:691–701, 1993.*
Chauveau, Nephrol. Dial. Transplant, 11[Suppl 4]:39–41, 1996.*
Kawasaki, in PCR Protocols, A Guide to Methods And Applications, Academic Press, Inc., pp. 146–152, 1990.*
Kwok et al. in Current Communications In Molecular Biology, Cold Spring Harbor Laboratory Press, pp. 151–158, 1989.*
Poiesz et al. in Current Communications In Molecular Biology, Cold Spring Harbor Laboratory Press, pp. 159–170, 1989.*
Higuchi, in PCR Technology, Principles and Applications for DNA Amplification, Stockton Press, pp. 31–37, 1989.*

* cited by examiner

*Primary Examiner*—James Martinell
(74) *Attorney, Agent, or Firm*—Christie, Parker & Hale, LLP

(57) ABSTRACT

A process is provided for preparing samples of blood, blood plasma, blood serum, or plasma proteins, including blood factor products, for PCR testing which minimizes contaminants which may interfere with the analysis. The process includes centrifugation of the initial sample to form a sample pellet, removing at least a portion of the supernatant from the pellet, and washing the pellet with an aqueous buffer. The buffer and washed pellet are then centrifuged, and a portion of the remaining supernatant is removed along with any contaminants contained therein. The clean, substantially contaminant-free pellet is then processed for PCR analysis.

48 Claims, No Drawings

PROCESS FOR PURIFICATION OF PCR TEST SAMPLES

FIELD OF THE INVENTION

The present invention relates to the removal of contaminants from PCR test sample preparations. More specifically, the present invention is directed to a process for the removal of viral fragments that could give a false positive PCR result and to the removal of interfering chemical reagents and molecules which could give a false negative result.

BACKGROUND OF THE INVENTION

Blood, plasma, and biological fluid donation programs are essential first steps in the manufacture of pharmaceutical and blood products that improve the quality of life and that are used to save lives in a variety of situations. Such products are used, for example, for the treatment of immunologic disorders, for the treatment of hemophilia and in maintaining and restoring blood volume in surgical procedures and other treatment protocols. The therapeutic uses of blood, plasma, and biological fluids require the donations of these materials be as free as possible from viral contamination. Typically, a serology test sample from each individual blood, plasma, or other fluid donation is tested for various antibodies, which are elicited in response to specific viruses, such as hepatitis C (HCV) and two forms of the human immunodeficiency virus (HIV-1 and HIV-2). In addition, the serology test sample may be tested for antigens designated for specific viruses such as hepatitis B (HBV), as well as antibodies elicited in response to such viruses. If the sample is serology positive for the presence of either specific antibodies or antigens, the donation is excluded from further use.

Whereas an antigen test for certain viruses, such as hepatitis B, is thought to be closely correlated with infectivity, antibody tests are not. It has long been known that a blood plasma donor may, in fact, be infected with the virus while testing serology negative for antibodies related to that virus. For example, a window exists between the time that a donor may become infected with a virus and the appearance of antibodies, elicited in response to that virus, in the donor' system. Therefore, tests directed to the detection of antibodies, may give a false indication for an infected donor if performed during the window period, i.e., the period between viral infection and the production of antibodies. Moreover, even though conventional testing for HBV includes tests for both antibodies and antigens, testing by more sensitive methods have confirmed the presence of the HBV virus in samples which were negative in the HBV antigen test. One method of testing donations, which have passed available antibody and antigen tests, in order to further ensure their freedom from incipient viral contamination, involves testing the donations by a polymerase chain reaction (PCR) method. PCR is a highly sensitive method for detecting the presence of specific DNA or RNA sequences related to a virus of interest in a biological material by amplifying the viral genome. Because the PCR test is directed to detecting the presence of an essential component of the virus itself, its presence in a donor may be found almost immediately after infection. There is, theoretically therefore, no window period during which a test may give a false indication of freedom of infectivity. A suitable description of the methodology and practical application of PCR testing is contained in U.S. Pat. Nos. 4,683,195, 4,683,202, and 5,176,995, the disclosures of which are expressly incorporated herein by reference.

Because of the exquisitely sensitive nature of the PCR test, with regard to identifying the presence of specific DNA or RNA sequences by amplifying the viral genome, PCR testing may give a false positive indication of viral activity even though no whole, i.e., infective, virus is present in the test sample. Viral genome amplification is able to occur even though the basis may merely be a number of viral fragments present in the test sample.

Commonly, blood products produced from plasma donations are subjected to a viral inactivation process before preparation of samples for PCR testing. Several well known methods are available for inactivating viruses, such as the use of solvent/detergent or heating the product to at least 60° C. for at least 10 hours. These methods, generally, are described as being capable of reducing the concentration of viruses by a number of "log units." For example, the solvent/detergent method is capable of reducing the viral contamination of the product (for example, hepatitis C) by at least $10^7$ per ml or "7 log units." Plasma products such as Factor VII Factor IX or prothrombin complex, which are derived from plasma donations, are routinely treated by heat treatment and/or the solvent/detergent method to inactivate any possible contaminating virus.

Although effective for inactivating viruses, such viral inactivation processes can result in fragmenting the whole virus, thereby rendering it non-infective while leaving the viral fragments in the product. This is particularly true when the product is heat-treated in the lyophilized state in the final container with no subsequent processing steps prior to its release. Thus, when the product is subjected to viral inactivation, particularly by heat-treatment, viral fragments remain in the product, along with the associated RNA or DNA, which may be amplified by the polymerase chain reaction. The amplification of the viral genome from non-infective viral fragments results in a false indication of viral contamination. In view of the foregoing, it can be seen that heat-treating a product for viral inactivation prior to PCR testing, but without removing the viral fragments, is not a preferred approach.

An additional source of uncertainty in PCR test results is caused by the fact that blood, plasma, serum, or blood product (such as Factor VIII or Factor IX or the like produced from blood or plasma) samples may contain significant concentrations of what might best be termed PCR inhibitors. (Both viral fragments and PCR inhibitors are referred to herein as "interfering contaminants" of the PCR process.) The most common PCR inhibitors include heme, heparin, metal ion chelators such as EDTA, and the like. Indeed, many samples are routinely collected in heparin, and it has been estimated that as much as 10% of the total sample population contains at least one form of PCR inhibitor.

Samples containing PCR inhibitors are potentially much more problematic than samples which contain significant concentrations of viral fragments. Although it is desirable to maximize the yield from a donation population, a false positive PCR viral indication would only result in one or a number of uncontaminated donations being excluded from the product stream. While very undesirable from an economic standpoint, this result does not add any substantial risk to the ultimate human consumers of the product stream. On the other hand, a false negative PCR viral indication caused by PCR inhibitors in a test sample would potentially allow a virally contaminated donation to enter the product stream.

Accordingly, in addition to removing viral fragments, a PCR sample preparation method will advantageously be able to remove PCR inhibitors as well.

SUMMARY OF THE INVENTION

A process for removing interfering contaminants, including PCR inhibitors and viral fragments, from blood protein-containing PCR assay samples is provided. The process includes the steps of introducing into a centrifuge tube an aqueous solution which comprises a blood protein and which also may include an infective virus and/or contaminants, such as viral fragments and/or PCR inhibitors in the form of soluble or suspendable chemical reagents or molecules, which interfere with the PCR assay. The aqueous blood protein solution is centrifuged to thereby separate the solution in the centrifuge tube into a supernatant which would contain potential contaminants and a solid pellet. The pellet will contain infective virus, if present, and/or insoluble protein or cellular debris or the like, depending on the nature of the sample. Substantially all of the supernatant is removed from the centrifuge tube without disturbing the pellet. An aqueous wash buffer solution is added to the centrifuge tube, thereby diluting the remaining supernatant so that potential interfering contaminants are in the diluted supernatant. The diluted supernatant is then centrifuged to provide a final supernatant and a washed pellet. A major portion of the final supernatant and any contaminants contained therein are removed from the centrifuge tube, while the residual supernatant and the washed pellet are recovered for PCR analysis.

DETAILED DESCRIPTION

The present invention is directed to a process for preparing and purifying samples intended for use with polymerase chain reaction (PCR) viral amplification test procedures, particularly samples of whole blood, blood plasma, serum, or blood products derived from plasma. Blood products with which the present invention may be advantageously used include, but are not limited to, albumin, Factor II, Factor VII, Factor VIII, Factor IX, Factor X and $X_a$, fibrinogen, antithrombin III, transferrin, haptoglobin, gamma globulins, fibronectin, protein C, protein S, α-1-proteinase inhibitor, $C_1$ esterase inhibitor, and thrombin.

GENERAL PROCEDURE FOR PREPARATION OF PCR SAMPLE

The sample to be tested via PCR, i.e., whole blood, blood plasma, serum, or a reconstituted lyophilized blood factor product which has been subjected to viral inactivation step is initially received by the laboratory for testing. The protein concentration of the product is determined using procedures well known in the art. If the sample is whole blood and an anticoagulant is present, the sample is initially subjected to a mild centrifugation, e.g., at 1500–1600×g for 5 minutes, and the supernatant plasma is then tested for protein concentration. If the sample is whole blood and no anticoagulant is present, the red blood cell clot is removed by a mild centrifugation, e.g., at 1500–1600×g for 5 minutes, and the supernatant serum is then tested for protein concentration. When the protein concentration of the sample is determined to be less than 6 grams per 100 ml of the sample solution, 1 ml of the product sample is admixed with 0.25 ml of molecular biology grade water in a centrifuge tube. When the protein concentration is determined to be greater than 6 grams per 100 ml of the sample solution, 0.5 ml of the product sample is admixed with 1 ml of molecular biology grade water in each of two tubes in order to adjust the protein concentration down to a value suitable for effective PCR testing (typically, in the range of from about 0.02 to about 0.05 gram/ml). The centrifuge tube is capped and then inverted several times to mix its contents, and the tube is then centrifuged under conditions sufficient to pelletize any virus which may be present and which is to be assayed via the PCR procedure. For example, when the viruses to be tested include hepatitis C, hepatitis B, and the human immunodeficiency viruses HIV-1 and HIV-2, it has been found that it is sufficient to centrifuge the tube at 23,000×g for 160 minutes at a temperature of about 16°±4° C. Of course, other time and g forces could be selected so long as it results in ensuring that the pellet contains the virus to be tested given the particular virus sedimentation rate and other factors. Upon centrifugation, the protein solution is separated into a supernatant which contains any soluble interfering contaminants that may be present and a pellet which contains any target virus which may be present, as well as insoluble protein and cellular debris and the like.

As much of the supernatant as possible is pipetted from the centrifuge tube without touching the bottom of the tube or disturbing the pellet. Typically, 10 μl to 20 μl of supernatant remains in the tube. An aqueous wash buffer solution is then added to the centrifuge tube containing the pellet. In a preferred embodiment, the buffer solution comprises 0.05 M sodium phosphate ($NaPO_4$) and 0.15 M sodium chloride (NaCl) at a pH in the range of from about 6 to about 8, and preferably, at about 6.8. In an exemplary embodiment, approximately 500 μl of the phosphate buffer is added gently down the side of the tube so as not to disturb the pellet. The addition of wash buffer dilutes the 10–20 μl of supernatant which remains in the tube so that interfering contaminants that may be present are in the diluted supernatant.

The diluted supernatant and associated pellet are then centrifuged at 23,000×g for about 30 minutes at a temperature of about 16°±4° C. This second centrifugation is done so that if the pellet had been inadvertently dislodged, it will be reaffixed to the bottom of the centrifuge tube.

It should be noted that while 16°±4° C. is a preferred sample temperature for the centrifugation step, temperatures in the range of from about 2° C. to about 37° C. are also suitable for practice of the present invention. However, care should be taken when the sample is at either of the aforementioned temperature extremes. In particular, temperatures in excess of 37° C. may cause any whole viruses that may be present in the sample to fragment or otherwise be degraded, for example, by the activity of proteases or nucleases that may be present in the sample. Both the degradation of the virus and the subsequent removal of the resulting degraded viral fragments in accordance with the process of the invention would increase the possibility of a false negative viral indication from any subsequent PCR test. On the other hand, if the ambient temperature is too cold, the biological material and any attendant viruses could freeze or crystallize, leading to equally disadvantageous PCR test results. Accordingly, while temperatures in the range of about 2° C. to about 37° C. are acceptable for practice of the present invention, a temperature of 16°±4° C. is preferred.

Following centrifugation, a major portion of the supernatant liquid is removed from the centrifuge tube. In an exemplary embodiment, about 80–90% of the supernatant liquid is removed from the tube, while the remaining 10–20% of the supernatant liquid and the pellet are then taken and resuspended for PCR analysis in accordance with well-understood and established PCR methodology.

The wash step of the present invention results in removal of possibly contaminating non-infective viral fragments and other possible interfering contaminants, such as the PCR inhibitors heparin, heme, EDTA, etc.

While a phosphate buffered saline washing solution is preferred, it will be understood that alternative washing solutions will be effective in practice of the present invention. In particular, pharmaceutical grade saline may be substituted for the phosphate buffered saline solution, as may Hanks Balance Salt Solution and the like. It is important, however, that the washing solution be able to hold viral fragments in suspension and, at the same time, provide a solvent for common classes of PCR inhibitors, such as heme, heparin, or metal ion chelators such as EDTA.

EXAMPLE 1

Preparation of Factor VIII Complex for PCR Testing with Solvent/Detergent and Heat-Treatment for Virus Inactivation In one exemplary embodiment of the practice of this invention, the starting material for providing the PCR sample of Factor VIII complex is cryoprecipitate which is contaminated with HIV virus. The cryoprecipitate is recovered from human blood plasma that has been collected and tested according to procedures approved by the U.S. Food and Drug Administration. The plasma is frozen at a temperature of about −20° C., and is subsequently thawed at 0° C. to 5° C. During the thawing process, a precipitate forms (the "cryoprecipitate"), which is removed by centrifugation and recovered for further purification and concentration.

In one embodiment, the cryoprecipitate is dissolved in a "heparin solution" which comprises distilled water containing from about 30 to 150 units of heparin per ml of water. The solution is then mixed at a temperature of from about 20° C. to about 30° C. until the cryoprecipitate is completely dissolved (approximately 10 minutes) to provide a cryoprecipitate/heparin solution. Preferably, the temperature during mixing is maintained at about 30° C., and the volume of heparin solution used is from about 2 to about 10 liters per kilogram of cryoprecipitate. After the cryoprecipitate is dissolved, the pH of the cryoprecipitate/heparin solution is adjusted to about 7±0.1 using, for example, 0.1 M HCl, and the solution is stirred for an additional 20 to 30 minutes.

Polyethylene glycol (PEG) powder, preferably having a molecular weight in the range of from about 2000 to about 6000 is then added to the cryoprecipitate/heparin solution to provide a PEG solution having a final PEG concentration of from about 1% to about 5% (wt/vol). The term "% (wt/vol)" as used herein means the weight of material added per 100 ml of starting volume of solution. The percentages referred to herein are all weight per volume unless otherwise indicated.

The addition of PEG to form the PEG solution results in precipitation of various proteins such as fibronectin and fibrinogen, leaving Factor VIII complex in solution. The fibronectin and other precipitated proteins, i.e., the PEG precipitate, are separated from the Factor VIII complex-containing solution (the PEG supernatant) by centrifugation. The PEG supernatant, i.e., the Factor VIII complex containing impure protein fraction, is recovered and processed further, in accordance with the process of this invention, to purify Factor VIII complex.

In one embodiment, a solution comprising both an organic solvent and a detergent is added to the PEG supernatant to inactivate virus that may be present. The amount of organic solvent and detergent added preferably results in a solution containing about 0.3% organic solvent and about 1% detergent. In an exemplary embodiment, the detergent is "Tween® 80" sold by Fisher Scientific, of Springfield, N.J., and the solvent is tri-n-butyl phosphate (TNBP).

The viral inactivated PEG supernatant solution, i.e., the Factor VIII complex containing impure protein fraction, is clarified by filtration and then further processed for purification of Factor VIII complex by affinity chromatography.

In an exemplary embodiment of the practice of this invention, Factor VIII complex solution from the viral inactivation step (the Factor VIII complex containing impure protein fraction) is applied to the chromatography column containing a heparin coupled chromatographic medium by pouring the solution through the column.

The heparin coupled chromatographic medium, with Factor VIII complex bound to it, is washed to remove all unbound proteins. In one embodiment, the washing is effected by applying about 5 to 10 volumes of a solution comprising about 0.01 to 0.05 M buffer, such as imidazole buffer, pH 6.5 to 7.5, containing about 0.1 M to 0.15 M of a salt solution, such as LiCl, NaCl, or KCl, and the effluent from the column is collected.

Factor VIII complex is eluted from the column, i.e., from the heparin coupled chromatographic medium, by applying to the column a buffered aqueous solution incorporating calcium, magnesium, strontium, or other divalent metal ion salt, such as $CaCl_2$, $MgCl_2$, $SrCl_2$, or the like. The column is washed with the buffered solution until all of the Factor VIII complex is washed from the column.

The Factor VIII complex eluted from the heparin coupled chromatographic medium is concentrated by ultrafiltration, approximately 20-fold, and the calcium concentration is reduced to from about 0.002 M to about 0.005 M. A histidine buffer and a glycine stabilizer are added to the ultrafiltered Factor VIII complex solution to provide histidine at a concentration of about 0.025 M and glycine at a concentration of about 0.28 M, and the pH is adjusted, using from about 1 M to about 6 M HCl, to approximately 7.3. The solution is then divided among separate vials, with each vial containing a desired number of units of Factor VIII:C activity. The solutions are then lyophilized to provide separate vials of purified Factor VIII complex concentrate.

The lyophilized Factor VIII preparation is subjected to dry heat treatment at 60° C. for 72 hours as a final viral inactivation step.

To provide a sample for PCR testing, the lyophilized Factor VIII concentrate is reconstituted with water for injection resulting in an aqueous solution which comprises Factor VIII and fragments of the now inactivated HIV virus and possible PCR inhibitors such as residual heparin.

The protein concentration of the lyophilized reconstituted Factor VIII is tested and found to be less than 6 grams per 100 ml of the sample solution. One ml of the product sample is admixed with 0.25 ml of molecular biology grade water in a centrifuge tube. The centrifuge tube is inverted several times to mix the materials together and is then centrifuged at 23,000×g for 160 minutes at a temperature of 16° C. A pellet containing insoluble protein is formed at the bottom of the centrifuge tube.

The supernatant is carefully pipetted from the centrifuge tube without touching the bottom of the tube while leaving approximately 20 μl of supernatant in the tube. 500 μl of phosphate buffered saline (0.05 M sodium phosphate ($NaPO_4$), and 0.15 M sodium chloride, pH 6.5) is gently added to the centrifuge tube down the side of the tube so as not to disturb the pellet. The tube containing the wash buffer and pellet is then ultracentrifuged at 23,000×g for 30 minutes at 16° C. Following centrifugation, a portion of the supernatant is removed from the tube leaving 100 μl (using the volume indicator on the side of the tube).

The sample is now ready for the first step of the PCR analysis, i.e., nucleic acid extraction. When nucleic acid extraction is to be started within 8 hours after the removal of the supernatant, the test samples are stored in 100 μl aliquots at 2° to 8° C. until the test procedure is to begin. If testing is not to be started within 8 hours, the samples are to be stored at −15° C. or colder. The frozen samples are then thawed just prior to testing.

EXAMPLE 2

Preparation of Serum for PCR Testing

A blood plasma donation which is contaminated with HIV virus is taken using procedures well known in the art, and serum is separated from the clotted red blood cells. A 4 ml sample of serum is provided for PCR testing for the HIV virus. Using procedures well known in the art, the protein concentration of the serum is determined to be greater than 6 grams per 100 ml. 0.5 ml of the serum sample is admixed with 1 ml of molecular biology grade water in each of two centrifuge tubes. The centrifuge tubes are inverted several times to mix the materials together and is then centrifuged at 23,000×g for 160 minutes at a temperature of about 16° C. to form a pellet containing the HIV virus at the bottom of each centrifuge tube.

As much of the supernatant as possible is pipetted from each centrifuge tube without touching the bottom of the tube. Approximately 20 μl of supernatant remain in the tube. 500 μl of phosphate buffered saline is gently added down the side of each centrifuge tube so as not to disturb the pellet. The tubes are ultracentrifuged at 23,000×g for 30 minutes at 16° C. After the second ultracentrifugation, the supernatant is pipetted, leaving 50 μl in each tube.

The samples in each tube are then combined into a single tube for a volume of 100 μl, and the sample is subjected to PCR analysis for HIV virus using standard PCR test procedures.

The above descriptions of exemplary embodiments of a process for preparing PCR test samples from whole blood, serum, plasma, plasma pools or plasma products, are for illustrative purposes. Because of variations which will be apparent to those skilled in the art, the present invention is not intended to be limited to the particular embodiments described above. For example, the process may be applied to samples which have not undergone a viral inactivation step. So long as the PCR sample preparation process includes a pellet, a wash, and subsequent removal of diluted supernatant, the invention can be practiced in the absence of any prior elements or steps disclosed above.

Accordingly, the present invention is not limited to the specific embodiments described herein, but rather as defined by the scope of the appended claims.

What is claimed is:

1. A process for removing interfering contaminants, including any viral fragments and PCR inhibitors that may be present, from blood protein containing samples which are to be tested via PCR assay for virus, the process comprising the steps of:

introducing an aqueous solution comprising a blood protein and any contaminants which may be present and which can interfere with the PCR assay into a centrifuge tube;

centrifuging the aqueous blood protein solution under conditions sufficient to pellet any infectious virus that may be present to thereby separate the solution in the centrifuge tube into a supernatant containing interfering contaminants and a pellet comprising such infectious virus;

removing substantially all of the supernatant from the centrifuge tube without disturbing the pellet;

adding an aqueous wash buffer solution to the centrifuge tube containing the pellet and remaining supernatant, the wash buffer selected so as to be able to hold viral fragments in suspension while providing a solvent for PCR inhibitors, and the wash buffer being added gently so as not to disturb the pellet while washing from the pellet surface any viral fragments that may have settled thereon, thereby diluting the remaining supernatant so that interfering contaminants including viral fragments are in the diluted supernatant;

centrifuging the centrifuge tube containing the pellet and the diluted supernatant under conditions sufficient to affix the pellet to the bottom of the centrifuge tube to thereby provide a final supernatant and a washed pellet;

removing a major portion of the final supernatant and the contaminants contained therein from the centrifuge tube and recovering the residual supernatant and the washed pellet for PCR analysis.

2. The process according to claim 1, wherein the buffer solution is a phosphate buffered saline solution comprising 0.05 M sodium phosphate and 0.15 M sodium chloride at a pH in the range of from 6 to 8.

3. The process according to claim 2, wherein the pH of the phosphate buffered saline solution is about 6.8.

4. The process according to claim 1 comprising, prior to the initial centrifugation step, the additional steps of:

estimating the protein concentration of the aqueous blood protein solution; and diluting the blood protein solution with water such that the estimated protein concentration of the diluted solution is within a range of from about 0.02 g/ml to about 0.05 g/ml.

5. The process according to claim 4, wherein, if the protein concentration of the blood protein solution is estimated to be greater than 6 grams/100 ml, 0.5 ml of the blood protein solution is admixed with 1.0 ml of water to thereby reduce the protein concentration.

6. The process according to claim 4, wherein, if the protein concentration of the blood protein solution is estimated to be less than 6 grams per 100 ml, 1 ml of the blood protein solution is admixed with 0.25 ml of water to thereby dilute the solution.

7. The process according to claim 1, wherein the aqueous blood protein solution is centrifuged at 23,000×g for 160 minutes to 190 minutes at 16±4° C.

8. The process according to claim 7, wherein the centrifuge tube containing the pellet and the diluted supernatant is centrifuged at 23,000×g for about 30 minutes at a temperature of about 16±4°C.

9. The process according to claim 1, wherein the blood protein is selected from the group consisting of albumin, Factor II, Factor VII, Factor VIII, Factor IX, Factor X and $X_a$, fibrinogen, antithrombin III, transferrin, haptoglobin, gamma globulin, fibronectin, protein C, protein S, α-1-proteinase inhibitor, $C_1$ esterase inhibitor, thrombin, and mixtures thereof.

10. The process according to claim 1, wherein the blood protein is derived from serum.

11. The process according to claim 1, wherein the blood protein is derived from whole blood.

12. The process according to claim 1, wherein the blood protein is derived from a plasma donation sample.

13. The process according to claim 12, wherein the plasma donation sample is taken from a pool formed from a multiplicity of plasma donations.

14. The process according to claim 1, wherein the interfering contaminants are viral fragments.

15. The process according to claim 1, wherein the interfering contaminants are soluble or suspendable chemical reagents or molecules.

16. The process according to claim 15, wherein the contaminant is heparin.

17. The process according to claim 15, wherein the contaminant is heme.

18. The process according to claim 1, wherein about 80–90% by volume of the final supernatant is removed from the washed pellet.

19. The process according to claim 1, wherein the sample to be tested via PCR for a virus is selected from the group consisting of HCV, HBV, HIV-1, and HIV-2.

20. A process for removing viral fragments from a blood protein-containing sample to be tested via PCR assay for virus, the process comprising the steps of:

introducing an aqueous solution comprising a blood protein and viral fragments into a centrifuge tube;

centrifuging the aqueous blood protein solution under conditions sufficient to pellet any infectious virus that may be present to thereby separate the solution in the centrifuge tube into a supernatant containing viral fragments and a pellet comprising such infectious virus;

removing substantially all of the supernatant and the viral fragments contained therein from the centrifuge tube without disturbing the pellet;

adding an aqueous wash buffer solution to the centrifuge tube containing the pellet and remaining supernatant, the wash buffer selected so as to be able to hold viral fragments in suspension, and the wash buffer being added gently so as not to disturb the pellet while washing from the pellet surface any viral fragments that may have settled thereon, thereby diluting the remaining supernatant so that viral fragments are in the diluted supernatant;

centrifuging the centrifuge tube containing the pellet and the diluted supernatant to thereby provide a final supernatant containing viral fragments and a washed pellet;

removing a major portion of the final supernatant and the viral fragments contained therein from the centrifuge tube and recovering the residual supernatant and the washed pellet for PCR analysis.

21. The process according to claim 20, wherein the aqueous wash buffer solution comprises 0.05 M sodium phosphate and 0.15 M sodium chloride at a pH in the range of from 6 to 8.

22. The process according to claim 20, wherein the pH of the aqueous wash buffer solution is about 6.8.

23. The process according to claim 20 comprising, prior to the initial centrifugation step, the additional steps of:

estimating the protein concentration of the aqueous blood protein solution; and diluting the blood protein solution with water such that the estimated protein concentration of the diluted solution is within a range of from about 0.02 g/ml to about 0.05 g/ml.

24. The process according to claim 23, wherein, if the protein concentration of the blood protein solution is estimated to be greater than 6 grams/100 ml, 0.5 ml of the blood protein solution is admixed with 1.0 ml of water to thereby reduce the protein concentration.

25. The process according to claim 23, wherein, if the protein concentration of the blood protein solution is estimated to be less than 6 grams per 100 ml, 1.0 ml of the blood protein solution is admixed with 0.25 ml of water to thereby dilute the solution.

26. The process according to claim 20, wherein the aqueous blood protein solution is centrifuged at 23,000×g for a period of from about 160 minutes to about 190 minutes, at a temperature of 16±4° C.

27. The process according to claim 26, wherein the centrifuge tube containing the pellet and the diluted supernatant is centrifuged at 23,000×g for about 30 minutes at a temperature of about 16±4° C.

28. The process according to claim 20, wherein the blood protein is selected from the group consisting of albumin, Factor II, Factor VII, Factor VIII, Factor IX, Factor X and $X_a$, fibrinogen, antithrombin III, transferrin, haptoglobin, gamma globulin, fibronectin, protein C, protein S, α-1-proteinase inhibitor, $C_1$ esterase inhibitor, thrombin, and mixtures thereof.

29. The process according to claim 26, wherein the blood protein is derived from a plasma donation sample.

30. The process according to claim 29, wherein the plasma donation sample is taken from a pool formed from a multiplicity of plasma donations.

31. The process according to claim 20, wherein the blood protein is derived from serum.

32. The process according to claim 20, wherein the blood protein is derived from whole blood.

33. The process according to claim 20, wherein the viral fragments to be assayed via PCR are selected from the group consisting of HCV, HBV, HIV-1, and HIV-2.

34. A process for removing PCR inhibitors from a blood protein-containing sample to be tested via PCR assay for virus, the process comprising the steps of:

introducing an aqueous solution comprising a blood protein and any PCR inhibitor that may be present into a centrifuge tube;

centrifuging the aqueous blood protein solution under conditions sufficient to pellet any infectious virus that may be present to thereby separate the solution in the centrifuge tube into a supernatant comprising the PCR inhibitor and a pellet comprising such infectious virus;

removing substantially all of the supernatant liquid from the centrifuge tube without disturbing the pellet;

adding an aqueous wash buffer solution to the centrifuge tube containing the pellet and remaining supernatant, the wash buffer selected so as to provide a solvent for the PCR inhibitor, and the wash buffer being added gently so as not to disturb the pellet, thereby diluting the remaining supernatant;

centrifuging the centrifuge tube containing the pellet and the diluted supernatant to thereby provide a final supernatant and a washed pellet;

removing a major portion of the final supernatant from the centrifuge tube and recovering the residual supernatant and the washed pellet for PCR analysis.

35. The process according to claim 34, wherein the buffer solution is a phosphate buffered saline solution comprising 0.05 M sodium phosphate and 0.15 M sodium chloride at a pH in the range of from 6 to 8.

36. The process according to claim 35, wherein the pH of the phosphate buffered saline solution is about 6.8.

37. The process according to claim 34 comprising, prior to the initial centrifugation step, the additional steps of:

estimating the protein concentration of the aqueous blood protein solution; and diluting the blood protein solution with water such that the estimated protein concentration of the diluted solution is within a range of from about 0.02 g/ml to about 0.05 g/ml.

38. The process according to claim 37, wherein, if the protein concentration of the blood protein solution is estimated to be greater than 6 grams/100 ml, 0.5 ml of the blood protein solution is admixed with 1.0 ml of water to thereby reduce the protein concentration.

39. The process according to claim 37, wherein, if the protein concentration of the blood protein solution is estimated to be less than 6 grams per 100 ml, 1.0 ml of the blood protein solution is admixed with 0.25 ml of water to thereby dilute the solution.

40. The process according to claim 34, wherein the aqueous blood protein solution is centrifuged at 23,000×g for a period of from about 160 minutes to about 190 minutes, at a temperature of 16±4° C., for preparing samples to be analyzed via PCR for HBV, HAV and HIV.

41. The process according to claim 34, wherein the centrifuge tube containing the pellet and the diluted supernatant is centrifuged at 23,000×g for about 30 minutes at a temperature of about 16±4° C.

42. The process according to claim 34, wherein the blood protein is selected from the group consisting of albumin, Factor II, Factor VII, Factor VIII, Factor IX, Factor X and $X_a$, fibrinogen, antithrombin III, transferrin, haptoglobin, gamma globulin, fibronectin, protein C, protein S, α-1-proteinase inhibitor, $C_1$ esterase inhibitor, thrombin, and mixtures thereof.

43. The process according to claim 34, wherein the blood protein is derived from serum.

44. The process according to claim 34, wherein the blood protein is derived from a plasma donation sample.

45. The process according to claim 34, wherein the blood protein is derived from whole blood.

46. The process according to claim 45, wherein the plasma donation sample is taken from a pool formed from a multiplicity of plasma donations.

47. The process according to claim 34, wherein about 80–90% by volume of the supernatant is removed from the washed pellet.

48. The process according to claim 34, wherein the virus to be assayed via PCR is selected from the group consisting of HCV, HBV, HIV-1, and HIV-2.

* * * * *

UNITED STATES PATENT AND TRADEMARK OFFICE
CERTIFICATE OF CORRECTION

PATENT NO.    : 6,348,336 B1
DATED         : February 19, 2002
INVENTOR(S)   : H. Edward Matveld, Lorraine B. Peddada, Andrew J. Conrad and Charles M. Heldebrant It is certified that error appears in the above-identified patent and that said Letters Patent is hereby corrected as shown below:

<u>Title page,</u>
Item [56], References Cited, U.S. PATENT DOCUMENTS, insert:
-- 5,418,130    5/23/95    Platz et al. ……………………….. 435/2
5,217,866       6/8/93     Summerton et al. …………….  435/6 --.
OTHER PUBLICATIONS, insert:
-- Dawson et al., in PCR Primer, A Laboratory Manual, eds. C.W. Dieffenbach and G.S. Dveksler, Cold Spring Harbor Laboratory Press, pages 79-97, 1995 --.

<u>Column 10,</u>
Line 18, replace "claim 26" with -- claim 20 --.

<u>Column 12,</u>
Line 12, replace "claim 45" with -- claim 44 --.

Signed and Sealed this

Eighth Day of October, 2002

*Attest:*

*Attesting Officer*

JAMES E. ROGAN
*Director of the United States Patent and Trademark Office*